(12) United States Patent
Itoh

(10) Patent No.: US 10,145,790 B2
(45) Date of Patent: Dec. 4, 2018

(54) IMAGE PROCESSING APPARATUS, IMAGE PROCESSING METHOD, IMAGE CAPTURING DEVICE AND STORAGE MEDIUM

(71) Applicant: CANON KABUSHIKI KAISHA, Tokyo (JP)

(72) Inventor: Yasuhiro Itoh, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/655,207

(22) Filed: Jul. 20, 2017

(65) Prior Publication Data

US 2018/0038789 A1     Feb. 8, 2018

(30) Foreign Application Priority Data

Aug. 8, 2016   (JP) ................. 2016-155791

(51) Int. Cl.
*G01N 21/47*     (2006.01)
*G06T 7/136*     (2017.01)
*G01N 15/02*     (2006.01)

(52) U.S. Cl.
CPC ......... *G01N 21/47* (2013.01); *G01N 15/0211* (2013.01); *G01N 15/0227* (2013.01); *G06T 7/136* (2017.01); *G01N 2021/473* (2013.01); *G01N 2021/4733* (2013.01)

(58) Field of Classification Search
CPC .............. G01N 21/47; G01N 15/0211; G01N 15/0227; G06T 7/136
See application file for complete search history.

(56) References Cited

U.S. PATENT DOCUMENTS

| 8,340,461 | B2 | 12/2012 | Sun et al. | |
| 9,558,580 | B2 | 1/2017 | Itoh | |
| 2006/0098973 | A1* | 5/2006 | Verdier | .................. G03B 17/18 396/291 |

(Continued)

OTHER PUBLICATIONS

Park et al, Single Image Haze Removal With WLS-Based Edge-Preserving Smoothing Filter, 2013, In Acoustics, Speech and Signal Processing (ICASSP), 2013 IEEE International Conference on, pp. 2469-2473.*

(Continued)

*Primary Examiner* — David F Dunphy
(74) *Attorney, Agent, or Firm* — Carter, DeLuca, Farrell & Schmidt, LLP

(57) ABSTRACT

An attempt is made to suppress the processing load while securing real-time properties of the image processing to improve visual recognizability of a captured image whose visual recognizability has been reduced by the influence of fine particle components. An image processing apparatus including: an extraction unit configured to extract an atmospheric light component from a captured image including an influence of fine particles in the atmosphere; and a removal processing unit configured to generate an image from the captured image, in which the influence of fine particles has been removed, based on the extracted atmospheric light component, and the extraction unit performs the extraction based on data of the captured image and data of an exposure value at the time of photographing the captured image.

8 Claims, 13 Drawing Sheets

(56) References Cited

U.S. PATENT DOCUMENTS

| | | | |
|---|---|---|---|
| 2006/0126959 A1* | 6/2006 | Padwick | G06K 9/0063 |
| | | | 382/254 |
| 2010/0040300 A1* | 2/2010 | Kang | G06K 9/00664 |
| | | | 382/255 |
| 2012/0154584 A1* | 6/2012 | Omer | G06T 5/008 |
| | | | 348/144 |
| 2014/0009683 A1* | 1/2014 | Yoshida | H04N 9/73 |
| | | | 348/655 |
| 2014/0072216 A1 | 3/2014 | Fang et al. | |
| 2015/0071563 A1* | 3/2015 | Park | G06T 5/007 |
| | | | 382/274 |
| 2015/0146980 A1* | 5/2015 | Itoh | G06K 9/4652 |
| | | | 382/167 |

OTHER PUBLICATIONS

He et al., "Guided Image Filtering," In ECCV 2010, Part I, LNCS 6311, European Conference on Computer Vision, Sep. 2010, pp. 1-14.

* cited by examiner

| Ev VALUE | -2 | -1 | 0 | 1 | ... | 14 | 15 | 16 | 17 |
|---|---|---|---|---|---|---|---|---|---|
| $Y_{th}$ | 180 | 200 | 220 | 230 | ... | 230 | 230 | 230 | 230 |

IMAGE PROCESSING APPARATUS, IMAGE PROCESSING METHOD, IMAGE CAPTURING DEVICE AND STORAGE MEDIUM

BACKGROUND OF THE INVENTION

Field of the Invention

The present invention relates to image processing to improve visual recognizability of a captured image by reducing the influence of fine particles in the atmosphere.

Description of the Related Art

In the field of a monitoring camera or the like, a reduction in visual recognizability due to fine particles (e.g., fog) present between a camera and a subject and a deterioration of image quality of a captured image have become problematic. As the cause of this, mention is made of scattering of light while traveling through the atmosphere. Then, it is known that there are two kinds of scattering of light due to fine particles in the atmosphere. One is Mie scattering, which occurs in the case where the diameter of a particle, such as trash, dust, and vapor, is great compared to the wavelength of light. In the case of the Mie scattering, light is scattered in white independently of the wavelength of the light and as a result of this, the farther a subject, the closer the color of the subject becomes white, and therefore, contrast is reduced. The other one is Rayleigh scattering, which occurs in the case where the diameter of a particle, such as an air molecule, is small compared to the wavelength of light. In the case of the Rayleigh scattering, the shorter the wavelength, the more scattering occurs. As a result of this, the farther a subject, the more the blue component is scattered, and therefore, the image becomes a bluish hue. The technique (haze removal technique) to remove a scattered light component from an image whose visual recognizability has been reduced due to occurrence of the above-described two kinds of scattering is proposed. In U.S. Pat. No. 8,340,461, the technique is disclosed which improves visual recognizability by calculating the minimum pixel value within the RGB channels in a predetermined peripheral range for each pixel of interest and by correcting contrast using an image (minimum value image) made up of the pixel with the minimum pixel value. Further, U.S. Patent Laid-Open No. 2014/072216 proposes a method of estimating light scattered while traveling through the atmosphere from a captured image by using the K-means method, which is one of the non-hierarchical clustering methods.

In the techniques described in U.S. Pat. No. 8,340,461 and U.S. Patent Laid-Open No. 2014/072216, the image processing to estimate the atmospheric light component, which is the scattered light component due to the atmosphere, is performed based on a captured image by a monitoring camera or a digital camera. Then, in the image processing, histogram processing, a processing of a plurality of threshold values, and so forth, are necessary for a photographed image. This processing needs to be performed across the entire image, and therefore, the processing load is heavy in the case where the processing is performed within a camera. Because of this, in the case where processing to remove the influence of fine particle components of the atmosphere is performed real time for a photographed image by making use of the techniques described in U.S. Pat. No. 8,340,461 and U.S. Patent Laid-Open No. 2014/072216, it is necessary to extend a dedicated circuit and the like for the above-described calculation within the image capturing device.

An object of the present invention is to make an attempt to suppress the processing load while securing real-time properties of the image processing to improve visual recognizability of a captured image whose visual recognizability has been reduced by the influence of fine particle components.

SUMMARY OF THE INVENTION

The image processing apparatus according to the present invention includes: an extraction unit configured to extract an atmospheric light component from a captured image including an influence of fine particles in the atmosphere; and a removal processing unit configured to generate an image from the captured image, in which the influence of fine particles has been removed, based on the extracted atmospheric light component, and the extraction unit performs the extraction based on data of the captured image and data of an exposure value at the time of photographing the captured image.

Further features of the present invention will become apparent from the following description of exemplary embodiments with reference to the attached drawings.

DESCRIPTION OF THE EMBODIMENTS

Hereinafter, with reference to the attached drawings, the present invention is explained in detail in accordance with preferred embodiments. Configurations shown in the following embodiments are merely exemplary and the present invention is not limited to the configurations shown schematically.

First Embodiment (Outline)

In the present embodiment, first, a Mie-scattered component and a Rayleigh-scattered component in an input image obtained by photographing a scene in which fog or the like occurs are found. Then, an image in which the influence of fine particles has been reduced is obtained by individually suppressing the Mie-scattered component and the Rayleigh-scattered component that are found and recombining both the components. More specifically, the procedure is as follow.

First, from a captured image in the RGB color space, which is an input image, a scattered component of light due to the atmosphere (atmospheric light component) is estimated. At the time of performing this estimation, the Ev value is made use of for the input image, which is the exposure value of a camera. Next, an image (scattered component enhanced image) in which the scattered light component in the input image is enhanced is found for each plane of RGB and for all RGB. Next, by using the scattered component enhanced image for each plane and the scattered component enhanced image for all RGB that are found, respectively, correction processing to remove the scattered component is performed for the input image. Then, by using the correction results, the above-described two kinds of scattered component are extracted. Finally, by recombining the Mie-scattered component and the Rayleigh-scattered component that are extracted in an arbitrary ratio, an image whose visual recognizability has been improved is obtained.

It is necessary to pay attention to that the Mie-scattered component and the Rayleigh-scattered component that are found by the above-described extraction or the arithmetic operation in the recombination processing in the present specification do not represent the Mie scattering and the Rayleigh scattering in the physical meaning in a strict and accurate manner. In the present specification, the Mie scattering mainly corresponds to the luminance change component by scattering and the Rayleigh scattering mainly corresponds to the color change component by scattering.

Figure 1:
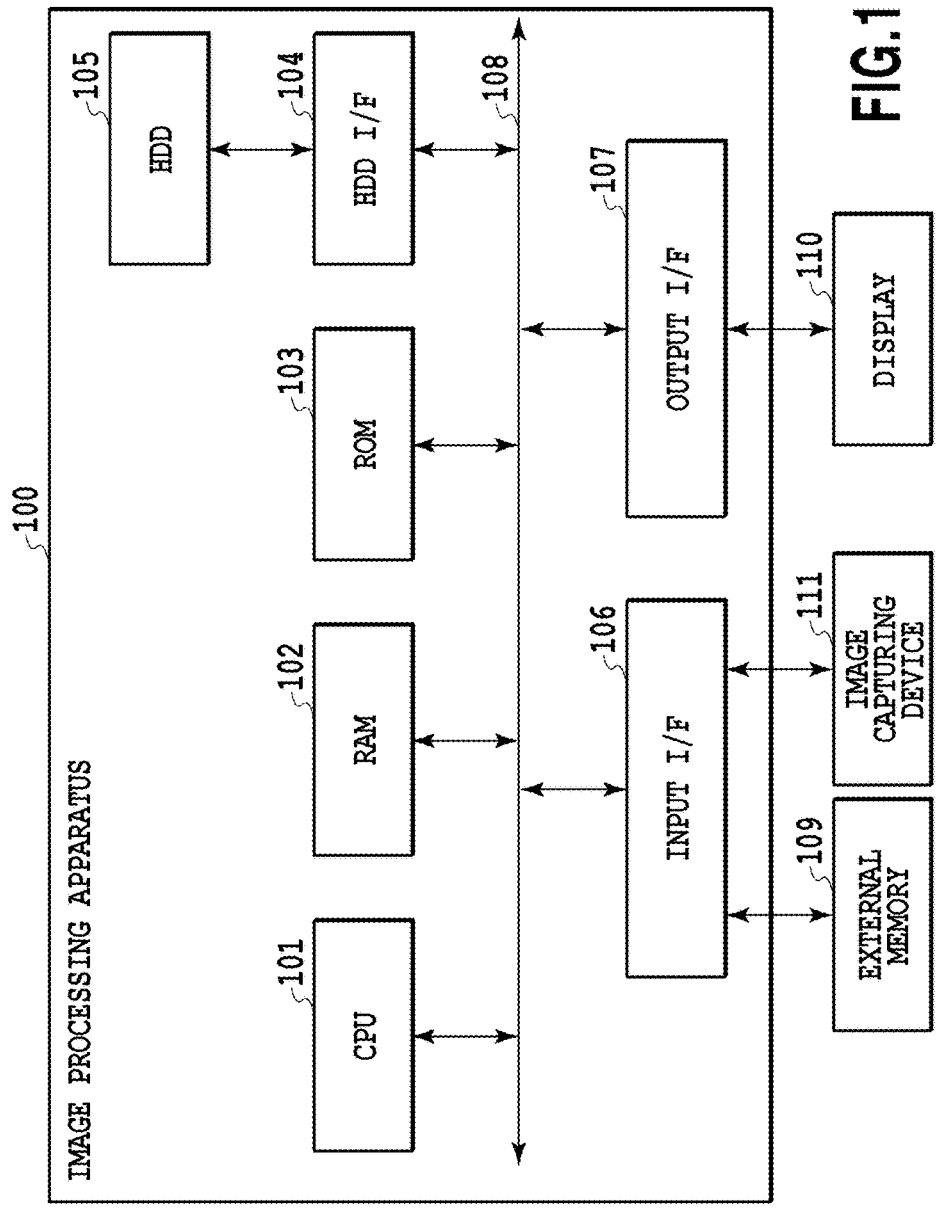
FIG. 1 is a block diagram showing an example of a configuration of an image processing apparatus.

FIG. 1 is a block diagram showing an example of a configuration of an image processing apparatus according to the present invention. An image processing apparatus 100 includes a CPU 101, a RAM 102, a ROM 103, an HDD I/F 104, an HDD 105, an input I/F 106, an output I/F 107, and a system bus 108 and to the image processing apparatus 100, an external memory 109, a display 110, and an image capturing device 111 are connected.

The CPU 101 executes programs stored in the ROM 103 by using the RAM 102 as a work memory and centralizedly controls each unit, to be described later, via the system bus 108. Due to this, various kinds of processing, to be described later, are performed.

The HDD I/F 104 is an interface, for example, such as a serial ATA (SATA), and is connected with the HDD 105 as a secondary storage device. Data is read from the HDD 105 and data is written to the HDD 105 via this HDD I/F 104. The secondary storage device may be a storage device, such as an optical disk drive, other than the HDD.

The input I/F 106 is a serial bus interface, for example, such as USB and IEEE 1394. Via this input I/F 106, data is acquired from the image capturing device 111, the external memory 109 (e.g., hard disc, memory card, CF card, SD card, USB memory), etc.

The output I/F 107 is a video output interface, for example, such as DVI and HDMI (registered trademark). Via this output I/F 107, an image or the like captured by the image capturing device 111 is displayed on the display 110 (various output devices, such as liquid crystal display).

The image capturing device 111 acquires digital data of a captured image by receiving light information on a subject by a sensor and performing A/D conversion. In the present embodiment, by the image capturing device 111 acquiring captured image data whose contrast has been reduced due to scattered light and by the image processing apparatus 100 performing image processing for the captured image data, an image in which the influence of fine particles has been reduced is generated. There exist components of the image processing apparatus 100 other than those described above, but they are not the main purpose of the present invention, and therefore, explanation is omitted.

Further, in the present embodiment, the image processing apparatus 100, the image capturing device 111, and the display 110 are configured as individual units, but the present invention is not limited to the configuration such as this. For example, it may also be possible to design a configuration in which all or part of the functions of the image processing apparatus 100 and the display 110 are incorporated in the image capturing device 111.

Figure 2:
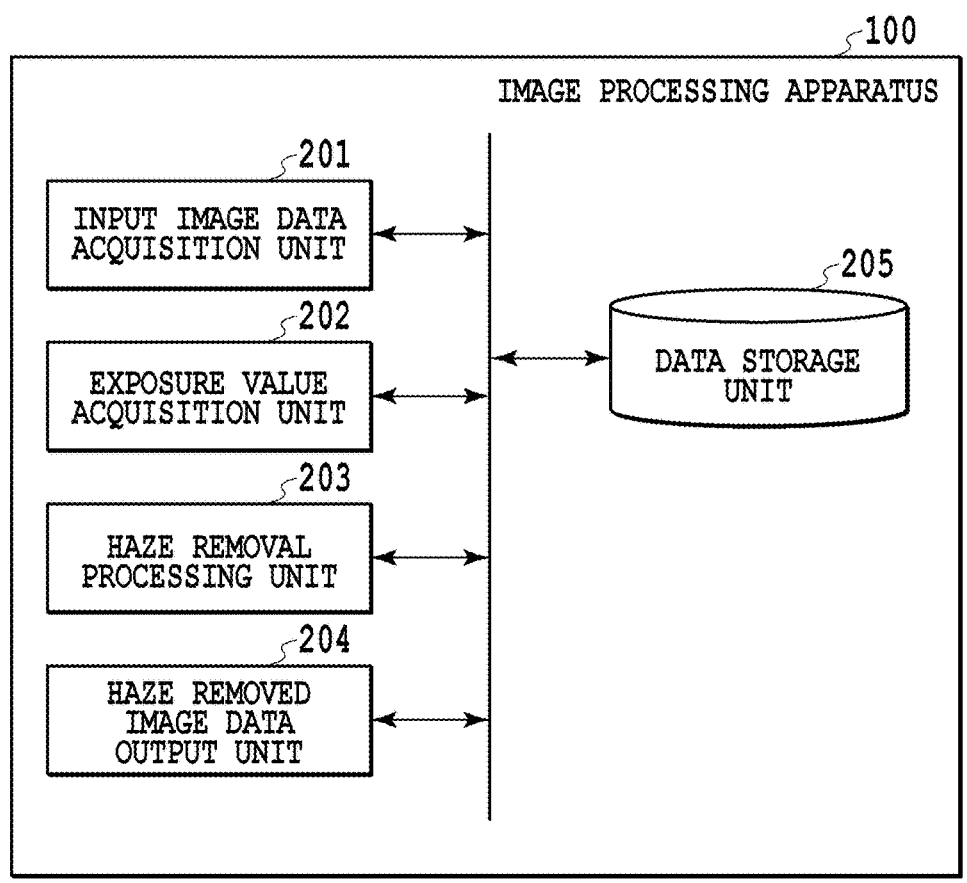
FIG. 2 is a function block diagram of the image processing apparatus.

FIG. 2 is a function block diagram of the image processing apparatus 100 according to the present embodiment and the image processing apparatus 100 includes an input image data acquisition unit 201, an exposure value acquisition unit 202, a haze removal processing unit 203, a haze removed image data output unit 204, and a data storage unit 205. The image processing apparatus 100 implements the function of each unit described above by loading a control program stored within the ROM 103 onto the CPU 101 and executing the control program. An outline of each unit is as follows.

The input image data acquisition unit 201 acquires an image in the RGB color space captured by the image capturing device 111 as an input image. The exposure value acquisition unit 202 acquires information on the exposure value (Ev value) in the input image. This Ev value is found by measurement using, for example, a sight meter (exposure meter) incorporated in the image capturing device 111. In the case where the sight meter or the like is used, for example, it may also be possible to find an average value of measurement results in the entire scene of the captured image or to find an average value in which the weights of the measurement results near the center of the scene are increased. Further, it may also be possible to find the Ev value from the pixel value of the input image data. The haze removal processing unit 203 generates an image (hereinafter, called "haze removed image") from the input image, whose visual recognizability has been improved by removing the scattered component of light due to fine particles in the atmosphere. The haze removed image data output unit 204 performs processing to output the data of the generated haze removed image to the outside, such as the display 110. The data storage unit 205 stores various kinds of data, such as processing results, generated in a generation process of the haze removed image, as well as storing the above-described various kinds of image data.

Figure 3:
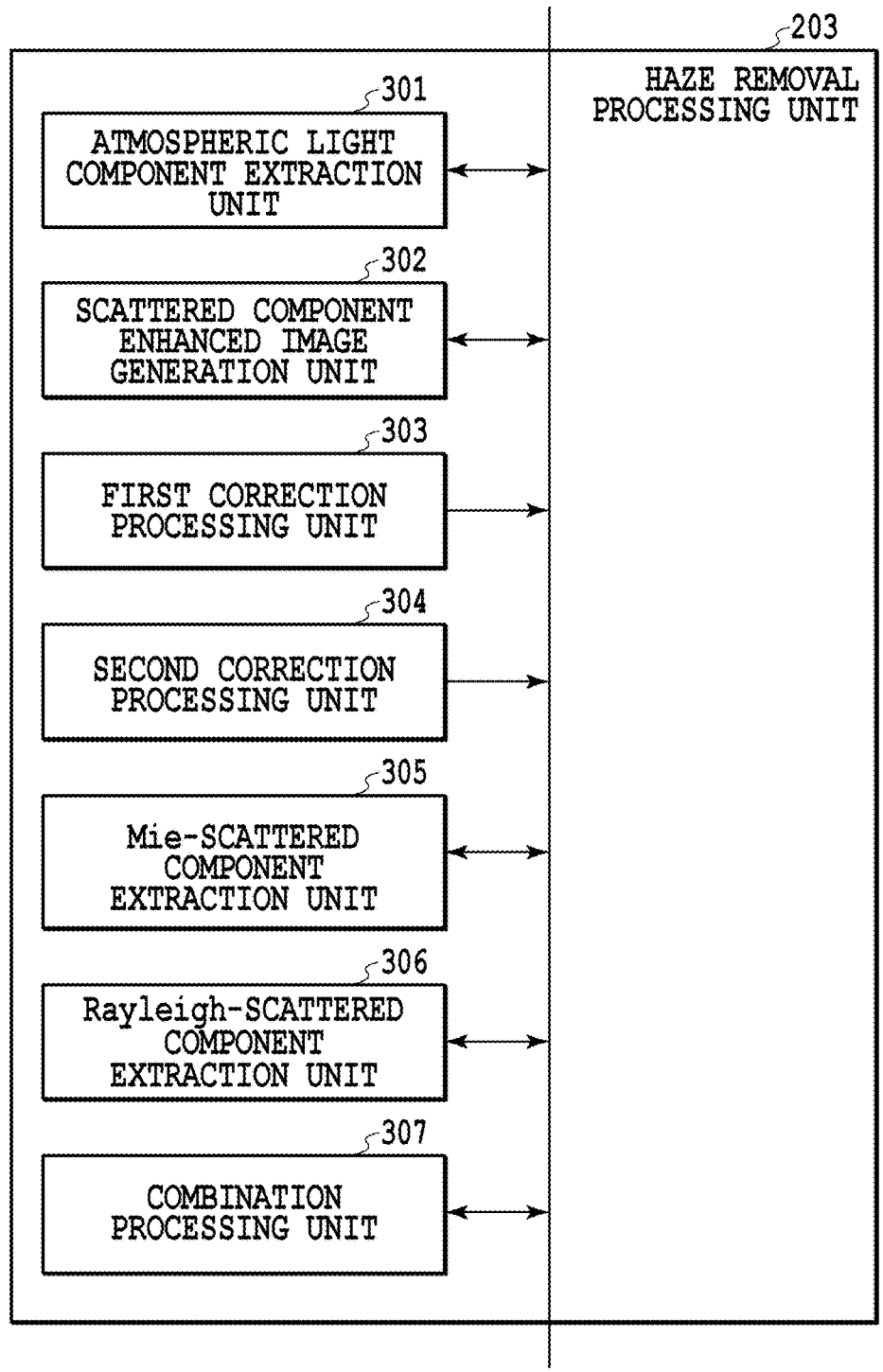
FIG. 3 is a diagram showing an internal configuration of a haze removal processing unit.

Following the above, the haze removal processing unit 203 that is a feature of the present invention is explained in detail. FIG. 3 is a diagram showing an internal configuration of the haze removal processing unit 203. The haze removal processing unit 203 includes an atmospheric light component extraction unit 301, a scattered component enhanced image generation unit 302, a first correction processing unit 303, a second correction processing unit 304, a Mie-scattered component extraction unit 305, a Rayleigh-scattered component extraction unit 306, and a combination processing unit 307.

Figure 4:
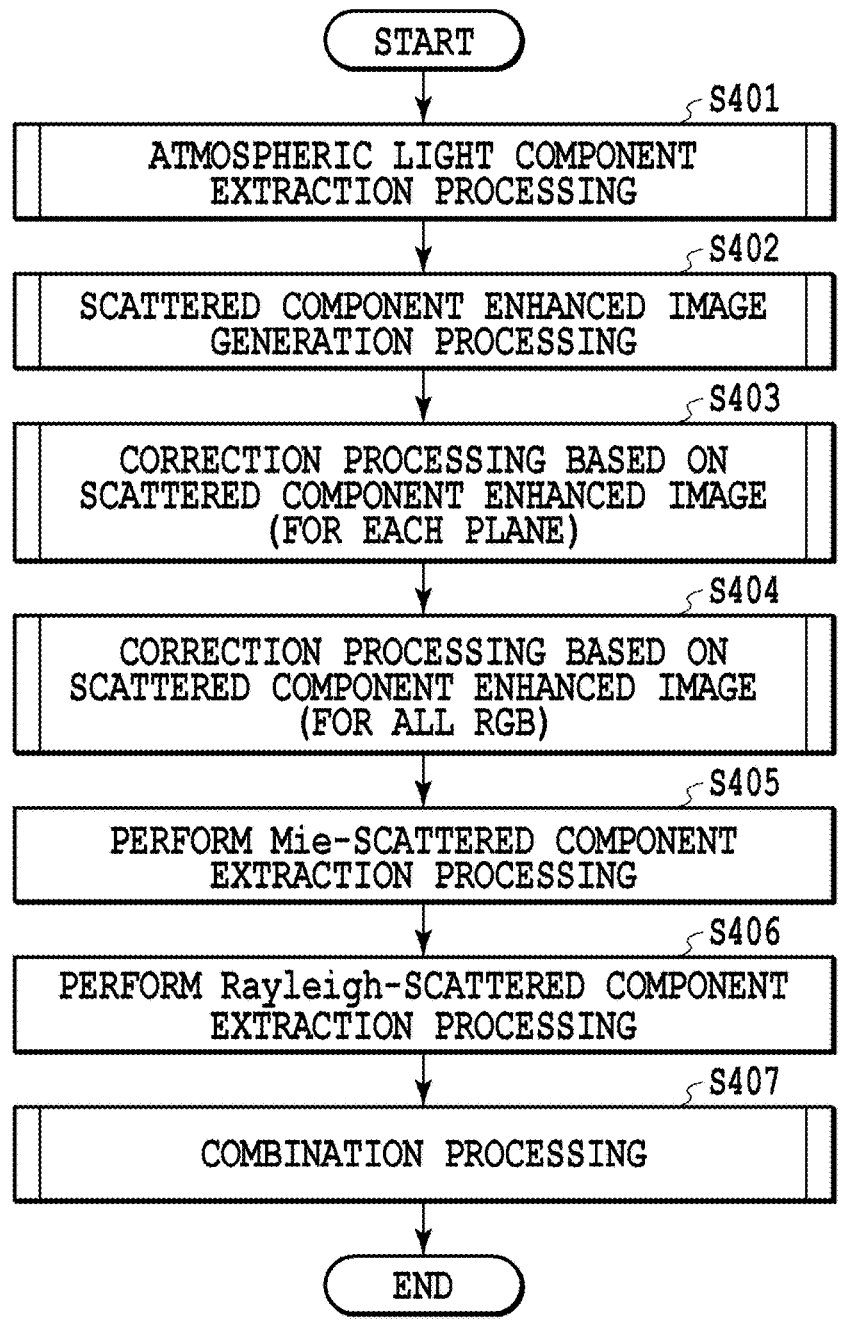
FIG. 4 is a flowchart showing a flow of processing in the haze removal processing unit.

Each unit described above making up the haze removal processing unit 203 is implemented by the CPU 101 loading a program held in the ROM 103 or the HDD 105 onto the RAM 102 and executing the program. FIG. 4 is a flowchart showing a flow of processing in the haze removal processing unit 203. In the following, in accordance with the flowchart in FIG. 4, the operation of the haze removal processing unit 203 is explained.

At step 401, the atmospheric light component extraction unit 301 performs processing to extract the atmospheric light component from an input image. The atmospheric light component means the component other than reflected light from an object in a captured image scene and includes the above-described Mie-scattered component and Rayleigh-scattered component. Then, at the time of extracting the atmospheric light component, the exposure value in the input image is used. Details of atmospheric light component extraction processing will be described later. Data of the extracted atmospheric light component is saved in the data storage unit 205 for processing at the subsequent steps.

At step 402, the scattered component enhanced image generation unit 302 generates the above-described scattered component enhanced image from the input image. The value of the pixel making up the scattered component enhanced image is determined based on a plurality of lower pixel values except for the minimum pixel value within a predetermined block, for example, by calculating a weighted average, and so forth. Then, the two kinds of scattered component enhanced image are generated, one for each plane and the other for all the RGB planes. By not using the minimum pixel value within the predetermined block at the time of the generation, a pixel having been affected largely by sensor noise is prevented from occurring. Details of scattered component enhanced image generation processing will be described later. Data of the generated two kinds of scattered component enhanced image is saved in the data storage unit 205 for processing at the subsequent steps.

At step 403, the first correction processing unit 303 performs correction processing (first correction processing) to remove the atmospheric light component corresponding to all the scattered light components from the input image by using the scattered component enhanced image for all RGB. Details of the first correction processing will be described later. Data of a corrected image (first corrected image) generated by the first correction processing is saved in the data storage unit 205 for processing at the subsequent steps.

At step 404, the second correction processing unit 304 performs correction processing (second correction processing) to remove the atmospheric light component corresponding to all the scattered light components from the input image by using the scattered component enhanced image for each plane. Details of the second correction processing will be described later. Data of a corrected image (second corrected image) generated by the second correction processing is saved in the storage unit 205 for processing at the subsequent steps.

At step 405, the Mie-scattered component extraction unit 305 extracts the Mie-scattered component by using the input image and the scattered component enhanced image for all RGB. Details of Mie-scattered component extraction processing will be described later. Data of the extracted Mie-scattered component is saved in the data storage unit 205 for processing at the subsequent steps.

At step 406, the Rayleigh-scattered component extraction unit 306 extracts the Rayleigh-scattered component by using the input image and the scattered component enhanced image for each plane. Details of Rayleigh-scattered component extraction processing will be described later. Data of the extracted Rayleigh-scattered component is saved in the data storage unit 205 for processing at the subsequent steps.

At step 407, the combination processing unit 307 performs combination processing to combine the Mie-scattered component and the Rayleigh-scattered component that are extracted in an arbitrary ratio into the above-described second corrected image. The combination processing is performed for each plane (details thereof will be described later). The combined image generated for each plane by the combination processing is integrated into one plane and after being saved in the data storage unit 205, is output to the outside as a haze removed image in accordance with the necessity.

The above is the flow of the processing in the haze removal processing unit 203. Following this, details of processing in each unit making up the haze removal processing unit 203 are explained.

(Extraction of Atmospheric Light Component)

Figure 5:
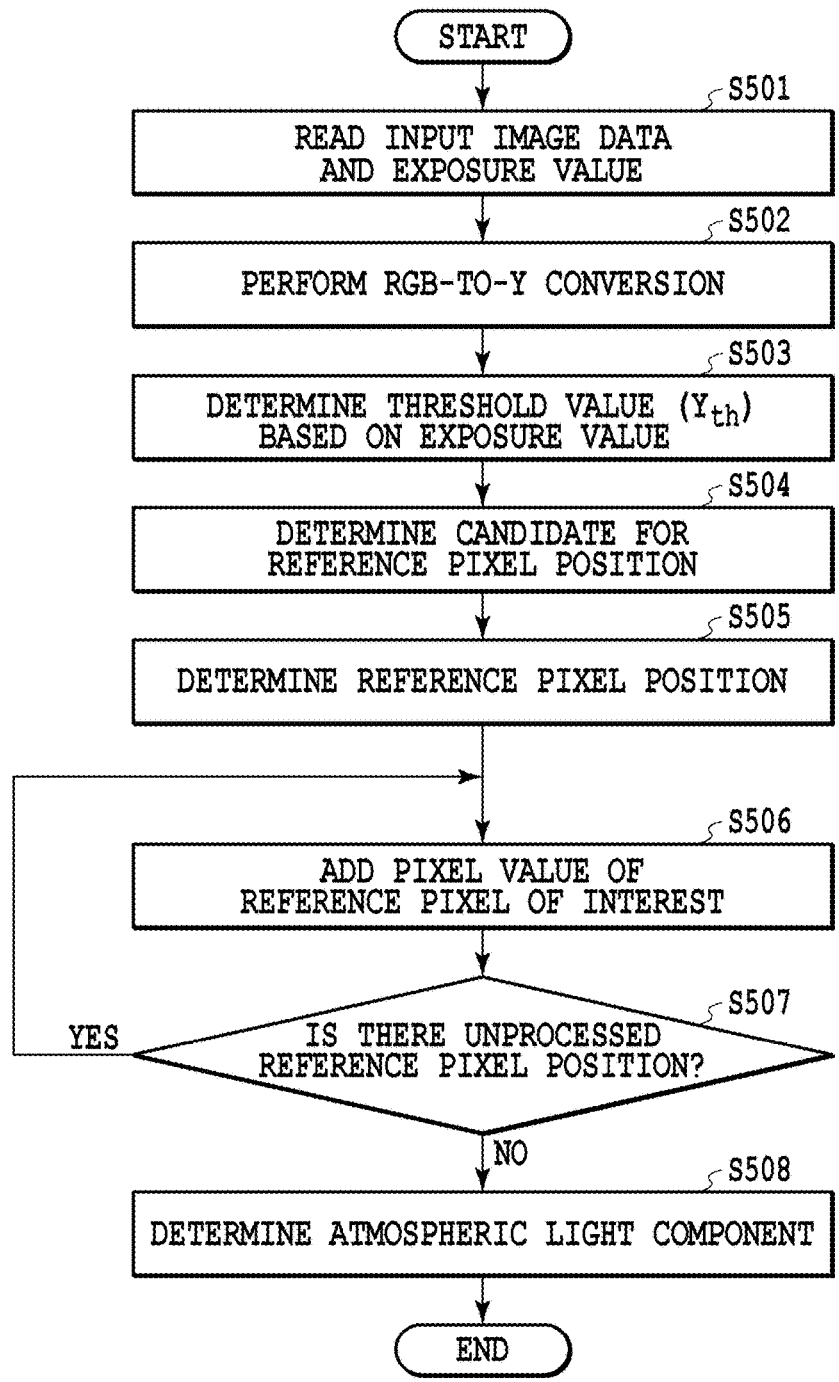
FIG. 5 is a flowchart showing details of extraction processing of an atmospheric light component.

The extraction processing (step 401) of the atmospheric light component in the atmospheric light component extraction unit 301 is explained. In the extraction (estimation) of the atmospheric light component of the present embodiment, first, based on the exposure value of an input image, the threshold value of luminance is found. Then, the input image (RGB image) is converted into a luminance image (Y image) and from pixels having a pixel value larger than or equal to the threshold value of luminance that is found as described above, a pixel to estimate the atmospheric light is determined by robust estimation processing. Then, based on the pixel value of the determined pixel, the atmospheric light is estimated. In the following, detailed explanation is given with reference to the flowchart in FIG. 5.

At step 501, image data in the RGB color space, which is the input image, and the exposure value (Ev value) in the input image are read from the data storage unit 205. At step 502 that follows, processing to convert the read RGB image into a Y image representing a luminance value is performed. For this conversion, it may be possible to apply a common RGB—Y color conversion expression.

Figures 6A, 6B:
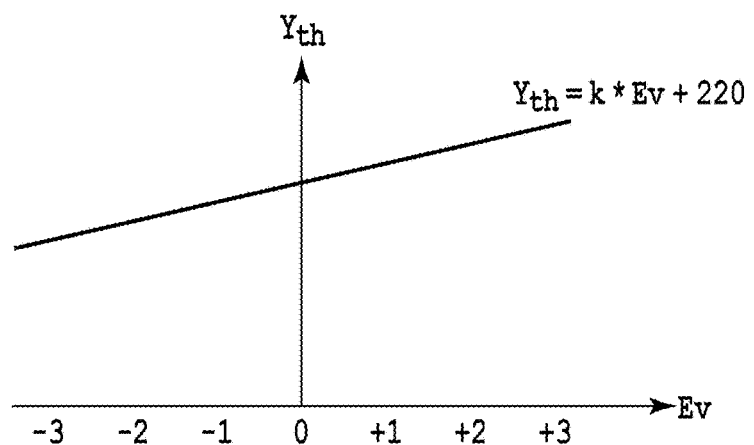
FIG. 6A is a table in which exposure values and predetermined threshold values are associated and FIG. 6B is a graph representing characteristics of a relational expression corresponding to the table.

At step 503, a threshold value ($Y_{th}$) of luminance is determined, which is used as a criterion at the time of determining a candidate (hereinafter, reference pixel position candidate) at a pixel position that is referred to in estimation of the atmospheric light component. Specifically, by referring to a table in which different exposure values (Ev values) are associated with respective corresponding threshold values ($Y_{th}$), the threshold value $Y_{th}$ corresponding to the Ev value read at step 501 is found. FIG. 6A shows an example of a table (LUT) in which exposure values and threshold values are associated. It is sufficient to determine the threshold value $Y_{th}$ in accordance with the Ev value of an input image by creating and holding the table such as this in advance. Further, instead of determining by using the table such as this, it may also be possible to determine by using a mathematical expression that specifies a relationship between the threshold value $Y_{th}$ of luminance and the exposure value as, for example, expression (1) below.

$$Y_{th} = k \times Ev + 220 \qquad \text{expression (1)}$$

FIG. 6B is a graph representing the characteristics of expression (1) described above. In expression (1) described above, $Y_{th} \leq Y_{MAX}$, and $Y_{MAX}$ represents the maximum value (in this example, 255) of luminance. Further, k is a constant and in this example, k is 20. In the case where a mathematical expression is used at the time of determining the threshold value $Y_{th}$ of luminance, the expression is not limited to expression (1) described above and another mathematical expression may be used. As described above, at the time of extracting the atmospheric light component from a captured image, a threshold value is determined, which is used as a criterion at the time of determining whether to employ as atmospheric light with reference to the exposure value at the time of image capturing. Conventionally, for example, a value is set as a threshold value, with which 1% of all the values from the largest value of all the pixel values of a captured image becomes eligible for a candidate of the pixel that is employed as the atmospheric light, but in this case, histogram processing, processing of a plurality of threshold values, and so forth, are necessary for the captured image, and therefore, the processing load is heavy. In the case of the method as described above, in which the threshold value is found from the exposure value, it is possible to considerably reduce the processing load. Further, information on the exposure value can be acquired easily from the pixel value of the captured image or by a sight meter incorporated in the image capturing device 111, and therefore, it is also possible to secure real-time properties of processing.

At step 504, the candidate (hereinafter, reference pixel position candidate) of the pixel position that is referred to at the time of estimating the atmospheric light component is determined based on the Y image obtained at step 502 and the threshold value $Y_{th}$ determined at step 503. Specifically, the position of the pixel having a value larger or equal to the threshold value $Y_{th}$ of all the pixel values of the Y image is determined to be the reference pixel position candidate.

At step 505, the pixel position that is referred to at the time of estimating the atmospheric light component is determined based on the reference pixel position candidate. Specifically, the actual reference pixel position is determined by using the robust estimation, such as the RANSAC method, for the reference pixel position candidates determined at step 504. It is desirable for the pixel to be selected as the atmospheric light component to be a pixel representing the portion of the sky. The purpose of this step is to exclude a high luminous pixel of the portion other than the sky, which is included in the reference pixel position candidate determined at step 504. Regarding this point, the percentage accounted for by the high luminous portion other than the sky on the input image is small and the luminance tends to differ from the color of the sky. Because of this, the robust estimation is performed, which can appropriately narrow down the reference pixels, by handling the pixel whose luminance is different of the pixels of the reference pixel position candidates as an outlier so as not to include the pixel as the reference pixel. At this time, it may also be possible to limit the number of pixels that are determined to be a reference pixel. The reason is to avoid the situation in which referring to too many pixels will result in that the sky including the change in color such as this becomes an estimation target because there is a case where the same sky has different colors (pixel values), for example, such as a case where the color of the sky is represented by gradation on the input image.

At step 506, processing to determine one pixel (reference pixel of interest) that is taken to be a target of the processing to estimate the atmospheric light component in accordance with the reference pixel position determined at step 505 and to add the pixel value of the reference pixel of interest for each color of RGB is performed. It may be possible to determine the reference pixel of interest by, for example, specifying the pixel whose pixel position is the uppermost top-left within the input image of the pixels determined to be the reference pixel as the first reference pixel of interest and then sequentially specifying the pixel on the right side (in the case where there is no pixel on the right side, then, the pixel in the next row) and so forth. The pixel value added for each color of RGB is held in the RAM 102 or the like.

At step 507, whether or not the addition processing has been completed for all the reference pixel positions determined at step 505 is determined. In the case where there is a reference pixel position for which the addition processing has not been performed yet, the processing returns to step 506 and the addition processing is continued by taking the pixel located at the next reference pixel position to be the reference pixel of interest. On the other hand, in the case where the addition processing has been completed for all the reference pixel positions, the processing advances to step 508.

At step 508, processing to average the accumulated added pixel values held in the RAM 102 or the like and to extract the atmospheric light component within the input image is performed. Specifically, by using expression (2) and expression (3) below, an atmospheric light component $A_{RGB}$ of an RGB image and an atmospheric light component $A_Y$ of a Y image are found, respectively.

$$A_{RGB} = (\Sigma A_R/n, \Sigma A_G/n, \Sigma A_B/n) \quad \text{expression (2)}$$

$$A_Y = (3 \times \Sigma A_R/n + 6 \times \Sigma A_G/n + \Sigma A_B/n)/10 \quad (3)$$

In expression (2) and expression (3) described above, $A_R$, $A_G$, and $A_B$ are values representing the atmospheric light component of the R plane, the G plane, and the B plane, respectively, $A_Y$ is a value representing the atmospheric light component of the Y image, and n represents the total number of reference pixels. The expression to find the atmospheric light component is not limited to expression (2) or expression (3) described above. For example, it may also be possible to obtain the atmospheric light component of the Y image by finding the minimum value of $\Sigma A_R/n$, $\Sigma A_G/n$, and $\Sigma A_B/n$.

Figure 7:
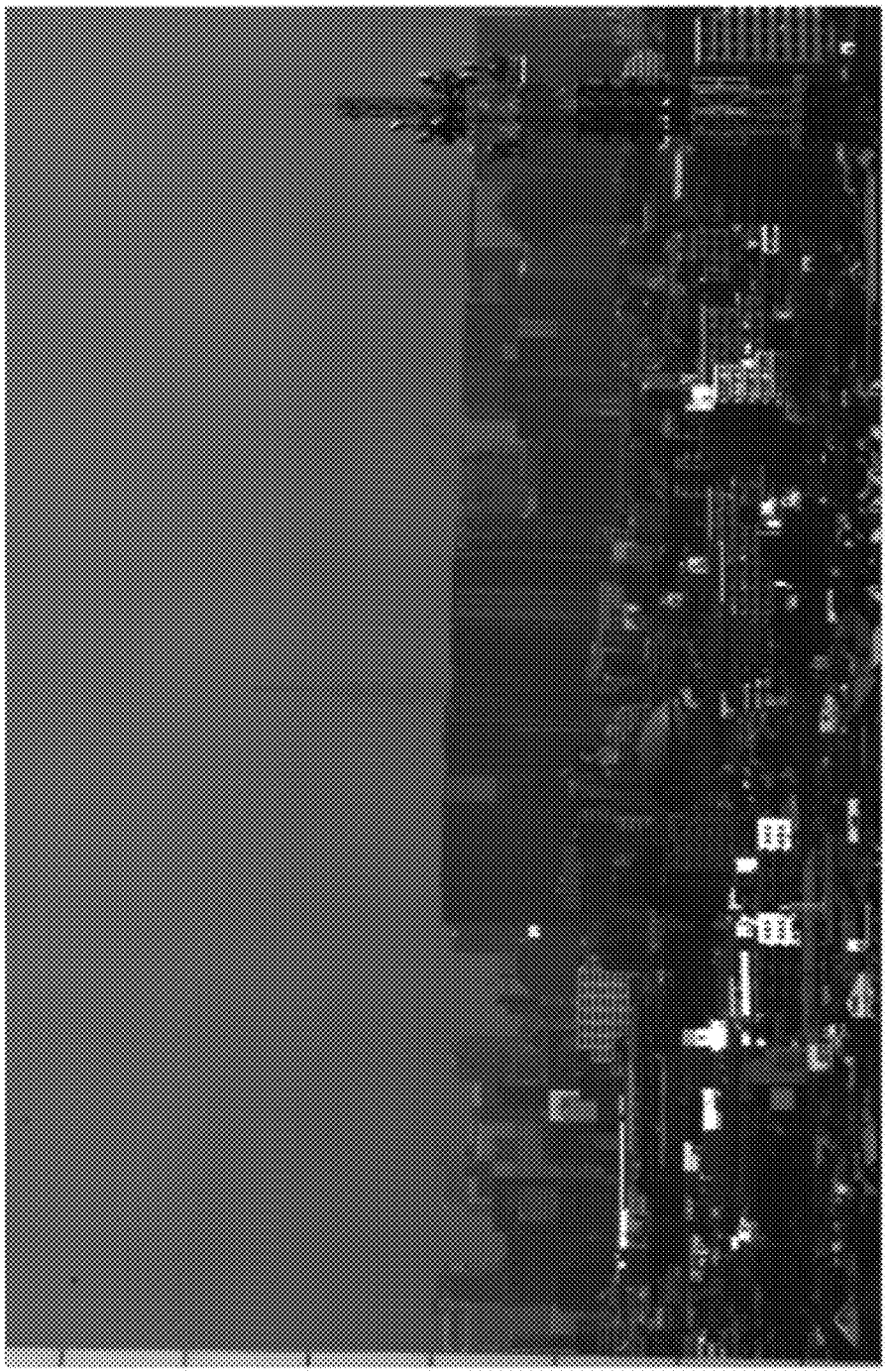
FIG. 7 is a diagram showing an example of an input image obtained by photographing a scene in which fog occurs.

As described above, the two kinds of atmospheric light component, i.e., $A_{RGB}$ and $A_Y$, within the input image are extracted in the atmospheric light component extraction unit 301. FIG. 7 is an example of an input image obtained by photographing a scene in which fog occurs and the atmospheric light component $A_{RGB}$ that is found from the input image (RGB image) such as this will be, for example, a value of (176, 177, 179).

(Generation of Scattered Component Enhanced Image)

The generation processing (step 402) of two kinds of scattered component enhanced image in the scattered component enhanced image generation unit 302 is explained with reference to FIGS. 8A and 8B. As described previously, the scattered component enhanced image includes two kinds of scattered component enhanced image: a scattered component enhanced image generated for each plane of RGB and a scattered component enhanced image for all RGB.

First, generation of a scattered component enhanced image for each plane is explained. FIG. 8A is a diagram explaining a generation process of a scattered component enhanced image for each plane. FIG. 8A is part of an arbitrary plane of an RGB image and a thick frame square 800 indicates a reference area corresponding to the predetermined block described previously. In this example, a center pixel 801 is taken to be a pixel of interest and an area (area of 3×3 pixels) consisting of nine pixels in total including the pixel of interest and eight pixels adjacent to the pixel of interest is taken to be a reference area, and a lower pixel value $T_{plane}$ corresponding to the pixel of interest 801 is derived. Here, it is possible to find the lower pixel value $T_{plane}$ in the pixel of interest 801 by, for example, calculating a weighted average of three lowest pixel values except for the minimum pixel value within the reference area 800. In this case, by taking the second lowest pixel value to be V_2, the third lowest pixel value to be V_3, and the fourth lowest pixel value to be V_4, and corresponding weight coefficients to be 2, 4, and 2, the lower pixel value $T_{plane}$ is expressed by expression (4) below.

$$T_{plane}=(2\times V\_2+4\times V\_3+2\times V\_4)/8 \qquad \text{expression (4)}$$

Figure 8A:
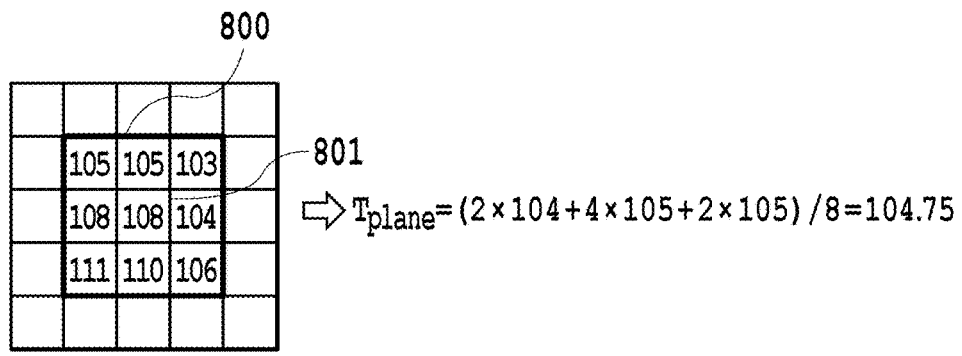
FIGS. 8A and 8B are diagrams explaining a generation process of a scattered component enhanced image.
Figure 8B:
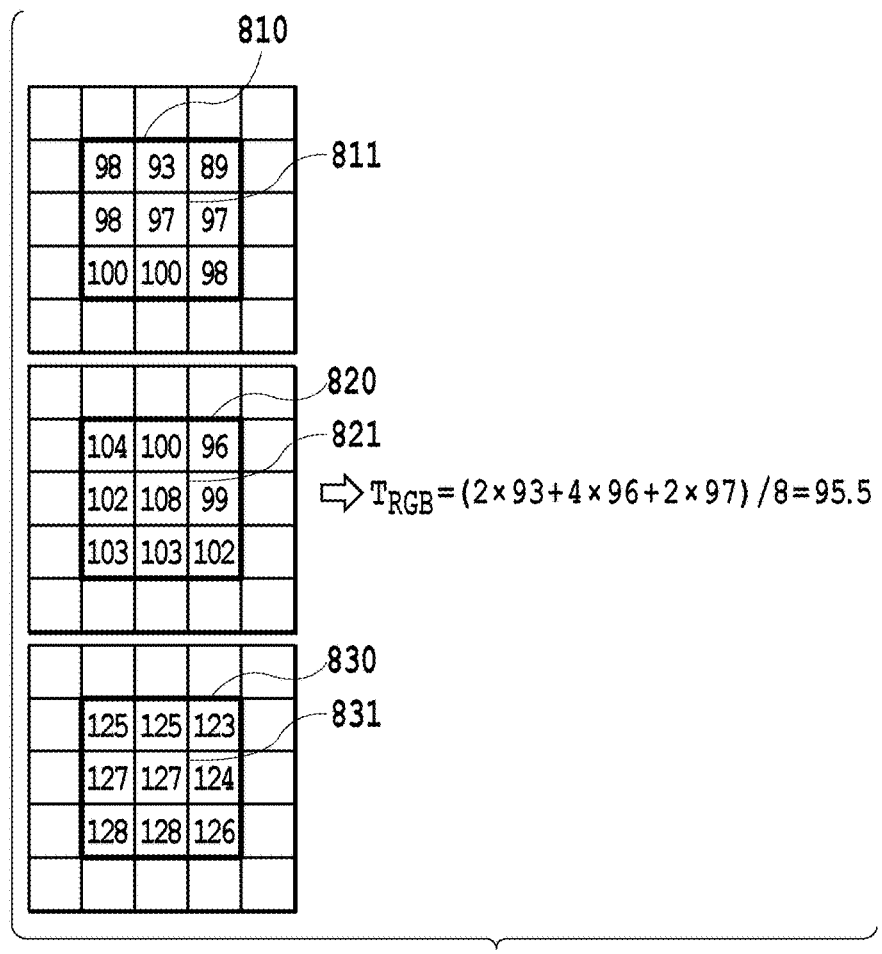

In the example in FIG. 8A, in the case where a weighted average of the three lower pixel values (right of the pixel of interest 801: 104, above the pixel of interest 801: 105, top-left of the pixel of interest 801: 105) except for the minimum pixel value "103" within the reference area 800 is found, the lower pixel value $T_{plane}$=104.75 is obtained. By performing the processing such as this for all the pixels of the target plane, the scattered component enhanced image for each plane is obtained. In this manner, by calculating the weighted average of a plurality of lower pixel values except for the minimum pixel value, the scattered component enhanced image for each plane is prevented from becoming one having been affected strongly by sensor noise. Then, the pixel that is used to derive the pixel value of the scattered component enhanced image is employed only from the plane of each color, and therefore, the scattered component enhanced image will be one that takes into consideration the influence of the wavelength of the scattering of light. Expression (4) described above is an example of the calculation expression at the time of finding the lower pixel value $T_{plane}$ corresponding to the pixel of interest and the calculation expression is not limited to this. For example, it may also be possible to find a weighted average of four or more lower pixel values except for the minimum value. Besides this, it may also be possible to convert the RGB value into the luminance value and then to find the lower pixel value in the luminance value after the conversion. Further, it may also be possible to find the lower pixel value by referring to a larger area by taking, for example, an area of 5×5 pixels with the pixel of interest as a center as a reference area corresponding to the predetermined block. At the time of determining the size of a reference area, it is considered to, for example, convert the RGB value into the luminance value and to increase the reference range for the larger luminance value. However, it is necessary to distinguish between the portion whose distance to a subject is short and the portion whose distance to a subject is long and there is a possibility that a white wall located near is determined erroneously to be the sky in the case where the reference range is large, and therefore, it is necessary to determine the reference range by taking into consideration the point such as this.

Next, the generation processing of a scattered component enhanced image for all RGB is explained. FIG. 8B is a diagram explaining a generation process of a scattered component enhanced image for all RGB. In FIG. 8B, part (same coordinates) of each plane of RGB is shown and each of thick frame squares 810, 820, and 830 indicates a reference area corresponding to the predetermined block. In the generation of the scattered component enhanced image for all RGB, each of center pixels 811, 821, and 831 having the same coordinates in three reference areas is taken to be the pixel of interest and the whole of the area including 27 pixels in total including adjacent eight pixels of each pixel of interest is taken to be a reference area. That is, for the scattered component enhanced image for all RGB, different from that for the scattered component enhanced image for each plane, the processing is performed by taking the pixels in all the planes, which are located around the three pixels of interest with the same coordinates, to be the reference area. Because of this, there is a possibility that the pixel that is employed is selected from among the pixels of all the RGB planes. In this manner, a lower pixel value $T_{RGB}$ corresponding to the pixels of interest 811, 821, and 831 with the same coordinates is derived. The lower pixel value $T_{RGB}$ at this time can also be found by expression (2) described above like the above-described lower pixel value $T_{plane}$. In the example in FIG. 8B, in the case where the weighted average of the three lower pixel values (above the pixel of interest 811: 93, top-right of the pixel of interest 821: 96, right of the pixel of interest 811: 97) except for the minimum pixel value "89" is found, the lower pixel value $T_{RGB}$=95.5 is obtained. In this manner, it is possible to obtain the scattered component enhanced image for all RGB.

(Generation of Corrected Image Based on Scattered Component Enhanced Image for all RGB)

Figure 9:
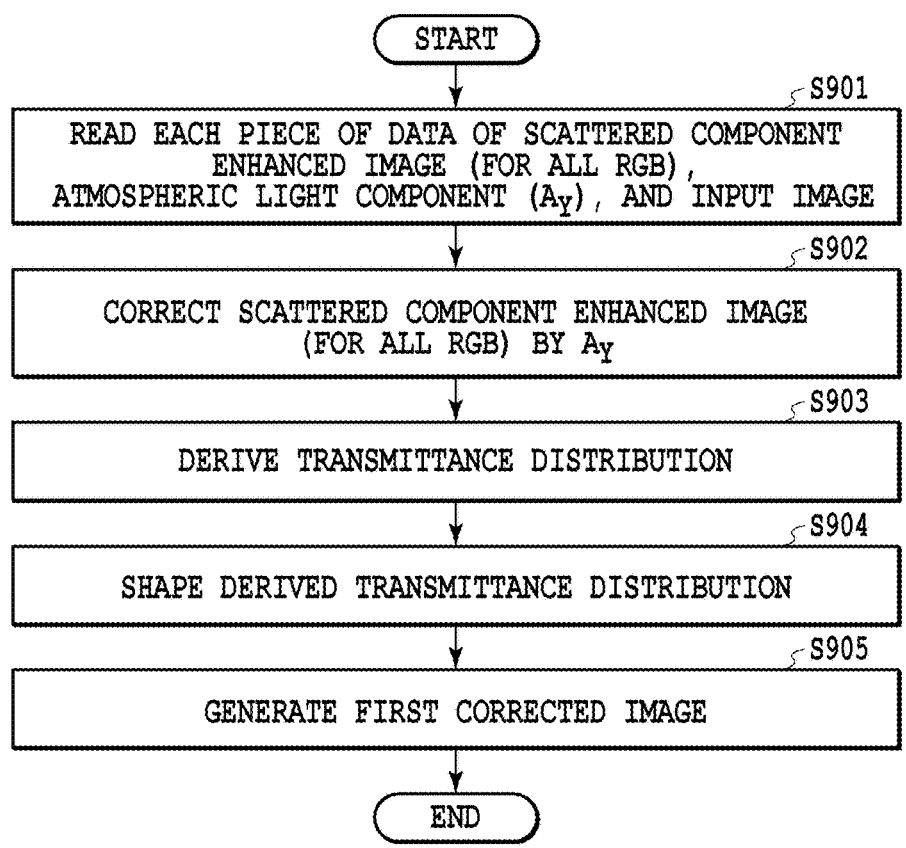
FIG. 9 is a flowchart showing details of correction processing to remove all scattered components from an input image based on a scattered component enhanced image for all RGB.

The correction processing (first correction processing: step 403) to remove all the scattered components from the input image based on the scattered component enhanced image for all RGB in the first correction processing unit 303 is explained with reference to the flowchart in FIG. 9.

At step 901, each piece of the data of the scattered component enhanced image for all RGB, the atmospheric light component of the Y image, and the input image is read from the data storage unit 205.

At step 902, by using the atmospheric light component $A_Y$ of the Y image, the scattered component enhanced image for all RGB is corrected. Specifically, by using expression (5) below, a corrected scattered component enhanced image for all RGB RGB_$A_Y$ is found.

$$RGB\_A_Y(x,y)=T_{in\_RGB}(x,y)/A_Y \qquad \text{expression (5)}$$

In expression (5) described above, $T_{in\_RGB}$ indicates the scattered component enhanced image for all RGB before the correction and (x, y) is the coordinates indicating the pixel position.

At step 903, a transmittance distribution $t_{RGB}$, (x, y) is derived based on the scattered component enhanced image for all RGB RGB_$A_Y$ after the correction by the atmospheric light component $A_Y$. Specifically, by applying expression (6) below to RGB_$A_Y$, $t_{RGB}$, (x, y) is found.

$$t_{RGB}(x,y)=1.0-\omega(RGB\_A_Y(x,y)) \qquad \text{expression (6)}$$

In expression (6) described above, w is a coefficient for adjustment provided to avoid the pixel value after the scattered component removal from becoming "0" because the transmittance becomes "0" in the case where the transmitted light of a target pixel is made up of only the light scattered by fine particles, such as fog, and the value of co is, for example, 0.9.

At step 904, the derived transmittance distribution $t_{RGB}$ (x, y) is shaped in accordance with the input image. This is processing to match the transmittance distribution $t_{RGB}$ (x, y) derived at step 803 with the shape of a subject, such as a structure, included in the scene of the input image. Specifically, the shape of a subject is separated by using, for example, the edge keep filter described in K. He, J. Sun, and X. Tang. Guided image filtering. In ECCV '10: European Conference on Computer Vision, pages 1-14, 2010.

At step 905, by using the atmospheric light component $A_Y$ of the Y image and the transmittance distribution $t_{RGB}$ (x, y) after the shaping, the processing to remove all the scattered components is performed for an input image I. Specifically, by using expression (7) below, an image (hereinafter, first corrected image) $J_{RGB}$ from which the scattered components have been removed is found.

$$J_{RGB}(x, y) = \frac{(I(x, y) - A_Y)}{\max(t_0, t_{RGB}(x, y))} + A_Y \qquad \text{expression (7)}$$

In expression (7) described above, $J_{RGB}$ (x, y) indicates the pixel value at the pixel position (x, y) of the first corrected image and I (x, y) indicates the pixel value at the pixel position (x, y) of the input image I. Further, to is a coefficient for adjustment provided to prevent the value of $J_{RGB}$ (x, y) from fluctuating considerably due to a slight difference in I (x, y) (shot noise or the like at the time of image capturing) in the case where the transmittance distribution $t_{RGB}$ (x, y) after the shaping is an infinitesimally small value. Specifically, the value of to is, for example, 0.1.

In this manner, the corrected image obtained by removing the scattered components from the input image is generated based on the scattered component enhanced image for all RGB.

(Generation of Corrected Image Based on Scattered Component Enhanced Image for Each Plane)

Figure 10:
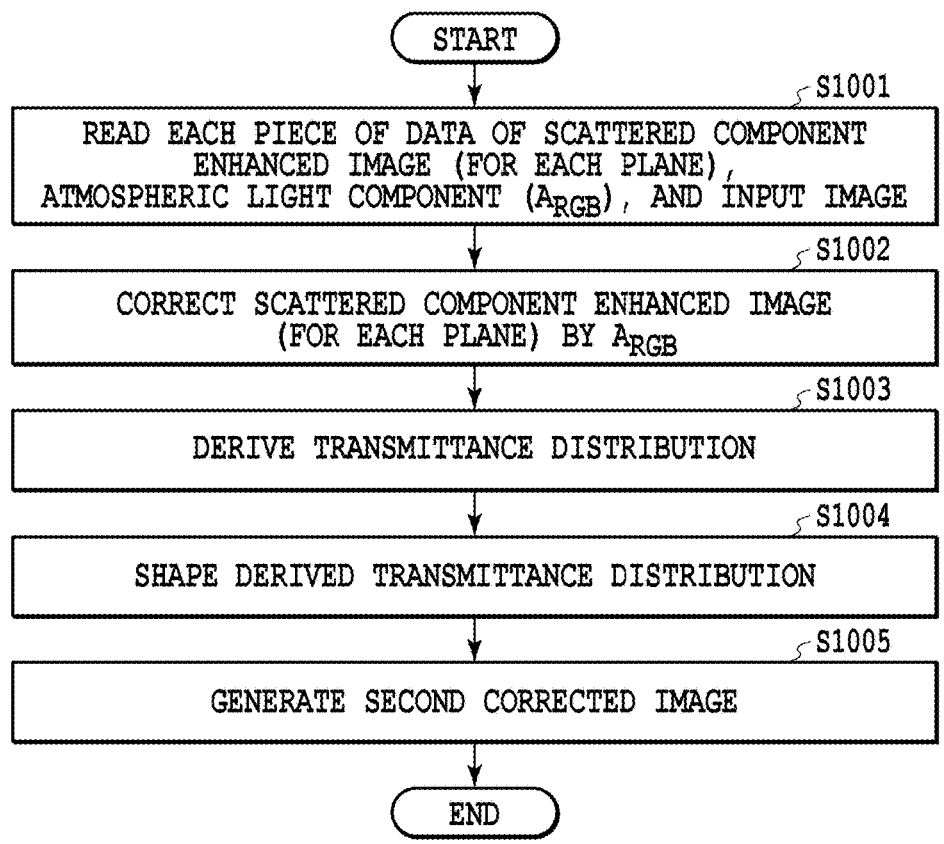
FIG. 10 is a flowchart showing details of correction processing to remove all scattered components from an input image based on a scattered component enhanced image for each plane.

The correction processing (second correction processing: step 405) to remove all the scattered components from an input image based on the scattered component enhanced image for each plane in the second correction processing unit 304 is explained with reference to the flowchart in FIG. 10.

At step 1001, each piece of the data of the scattered component enhanced image for each plane, the atmospheric light component of the RGB image, and the input image is read from the data storage unit 205.

At step 1002, by using the atmospheric light component $A_{RGB}$ of the RGB image, the scattered component enhanced image for each plane is corrected. Specifically, by using expression (8) below, a corrected scattered component enhanced image for each plane Plane_$A_{RGB}$ is found.

$$\text{Plane}\_A(x,y,c) = T_{in\_plane}(x,y,c)/A_{RGB} \qquad \text{expression (8)}$$

In expression (8) described above, $T_{in\_plane}$ indicates the scattered component enhanced image for each plane before the correction and (x, y, c) is coordinates indicating the pixel position in a color plane c. In this case, the value of c and each plane are associated with each other in such a manner that c=1 is associated with an R image, c=2 with a G image, and c=3 with a B image.

At step 1003, based on the scattered component enhanced image for each plane Plane_$A_{RGB}$ after the correction by the atmospheric light component $A_{RGB}$, a transmittance distribution $t_{plane}$ (x, y, c) is derived. Specifically, by applying expression (9) below to Plane_$A_{RGB}$, $t_{plane}$ (x, y, c) is found.

$$t_{plane}(x,y,c) = 1.0 - \omega(\text{Plane}\_A_{RGB}(x,y,c)) \qquad \text{expression (9)}$$

In expression (9) described above, as in expression (6) described previously, ω is a coefficient for adjustment provided to avoid the pixel value after the scattered component removal from becoming "0" and the value of ω is, for example, 0.9.

At step 1004, the derived transmittance distribution $t_{plane}$ (x, y, c) is shaped in accordance with the input image. The specific procedure is the same as that at step 904 described previously. In the case of the scattered component enhanced image for each plane, shaping to separate the shape of a subject is performed for each plane, i.e., shaping is performed by changing c in the transmittance distribution $t_{plane}$ c).

At step 1005, by using the atmospheric light component $A_{RGB}$ of the RGB image and the transmittance distribution $t_{plane}$ (x, y, c) after the shaping, processing to remove all the scattered components is performed for the input image I. Specifically, by using expression (10) below, an image (hereinafter, second corrected image) $J_{plane}$ from which the scattered components have been removed is found.

$$J_{plane}(x, y, c) = \frac{(I(x, y, c) - A_{RGB})}{\max(t_0, t_{plane}(x, y, c))} + A_{RGB} \qquad \text{expression (10)}$$

In expression (10) described above, $J_{plane}$ (x, y, c) indicates the pixel value at the pixel position (x, y, c) of the second corrected image and I (x, y, c) indicates the pixel value at the pixel position (x, y, c) of the input image I. Further, to is an adjustment coefficient as in expression (7) described above, and the value of to is, for example, 0.1.

In this manner, based on the scattered component enhanced image for each plane, the corrected image obtained by removing the scattered components from the input image is generated for each plane.

(Extraction of Mie-Scattered Component)

The extraction processing (step 405) of the Mie-scattered component in the Mie-scattered component extraction unit 305 is explained. The Mie-scattered component is the luminance change component by scattered light and corresponds to that obtained by removing the first corrected image $J_{RGB}$ described above from the input image I. Specifically, it is possible to find a Mie-scattered component M by, for each pixel of the input image I, performing subtraction of the pixel value for each plane of each of RGB by using expression (11) and then finding the maximum value in each plane by using expression (12) and integrating them into one plane.

In the case where $I(x,y,c) - J_{RGB}(x,y) \geq 0 : M(x,y,c) = I(x,y,c) - J_{RGB}(x,y)$ In the case where $I(x,y,c) - J_{RGB}(x,y) < 0 : M(x,y,c) = 0$ expression (11)

$$M(x,y) = \max(M(x,y,c)) \qquad \text{expression (12)}$$

Figure 11:
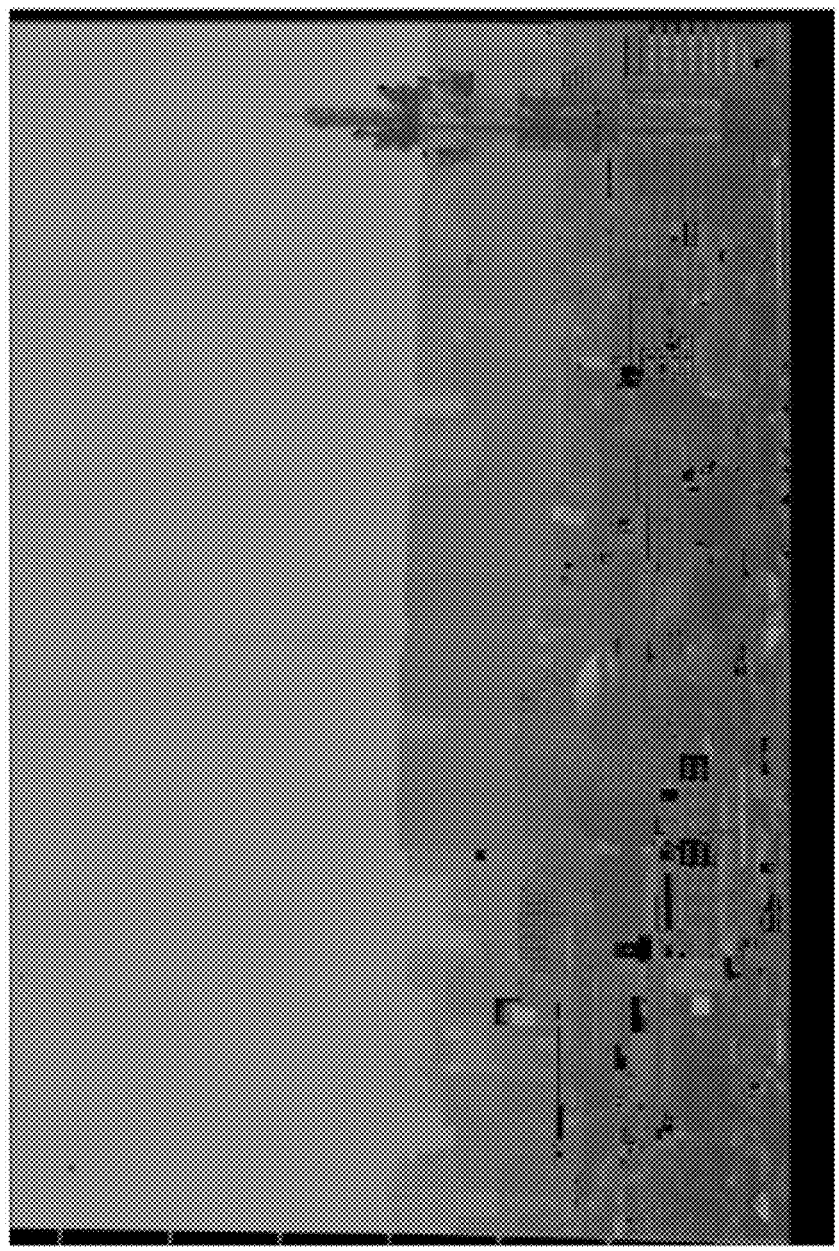
FIG. 11 is an example of an image showing a component corresponding to Mie scattering extracted from an input image.

The meanings of (x, y, c) and (x, y) in expression (11) and expression (12) described above are the same as those in expression (7) and expression (8) described previously. FIG. 11 is an image representing the component M corresponding to the Mie scattering obtained from the input image in FIG. 7. In this manner, the Mie-scattered component is extracted from the input image.

It may also be possible to use expression (11)' below in place of expression (11) described above.

In the case where $I(x,y,c) - J_{plane}(x,y,c) \geq 0 : M(x,y,c) = I(x,y,c) - J_{plane}(x,y,c)$ In the case where $I(x,y,c) - J_{plane}(x,y,c) < 0 : M(x,y,c) = 0$ expression (11)'

(Extraction of Rayleigh-Scattered Component)

The extraction processing (step 406) of the Rayleigh-scattered component in the Rayleigh-scattered component extraction unit 306 is explained. The Rayleigh-scattered component is the color change component by scattered light and corresponds to that obtained by removing the second corrected image $J_{plane}$ and the Mie-scattered component M described above from the input image I. Consequently, it is possible to find a Rayleigh-scattered component R by performing subtraction of the pixel value by using expression (13) below for each pixel of the input image I.

In the case where $I(x,y,c)-J_{plane}(x,y,c)-M(x,y) \geq 0$: $R(x,y,c)=I(x,y,c)-J_{plane}(x,y,c)-M(x,y)$ In the case where $I(x,y,c)-J_{plane}(x,y,c)-M(x,y)<0$: $R(x,y,c)=0$ expression (13)

Figure 12:
FIG. 12 is an example of an image showing a component corresponding to Rayleigh scattering extracted from an input image.

The meanings of (x, y, c) and (x, y) in expression (13) described above are the same as those in expression (7) and expression (8) described previously. FIG. 12 is an image representing the component corresponding to the Rayleigh scattering obtained from the input image in FIG. 7. In this manner, the Rayleigh-scattered component is extracted from the input image.

(Combination Processing)

Finally, processing to recombine the Mie-scattered component and the Rayleigh-scattered component that are extracted with the second corrected image generated for each plane in an arbitrary ratio in the combination processing unit 307 is explained. Specifically, a combined image $J_{comb}$ is found for each plane by performing addition of the pixel value by using expression (14) below for each pixel of the second corrected image $J_{plane}$.

$$J_{comb}(x,y,c)=J_{plane}(x,y,c)+m \cdot M(x,y)+r \cdot R(x,y,c) \quad \text{expression (14)}$$

In expression (14) described above, m is an intensity coefficient by which the Mie-scattered component is multiplied and r is an intensity coefficient by which the Rayleigh-scattered component is multiplied and it is desirable for r and m to take a value between 0 and 1, respectively, for example, r=0.5 and m=0.1. Further, by setting m=0 and r=0, it is possible to obtain an image specialized only in improvement of contrast and which does not take coloring into consideration. Further, by putting r close to 1, there is a tendency for the coloring after the processing to decrease and by putting m close to 1, there is a tendency for the removal intensity of fog to decrease and for the contrast to decrease. In this manner, by performing image combination while arbitrarily changing the values of m and r, it is possible to control the degree of the influence by scattering of light.

Figure 13:
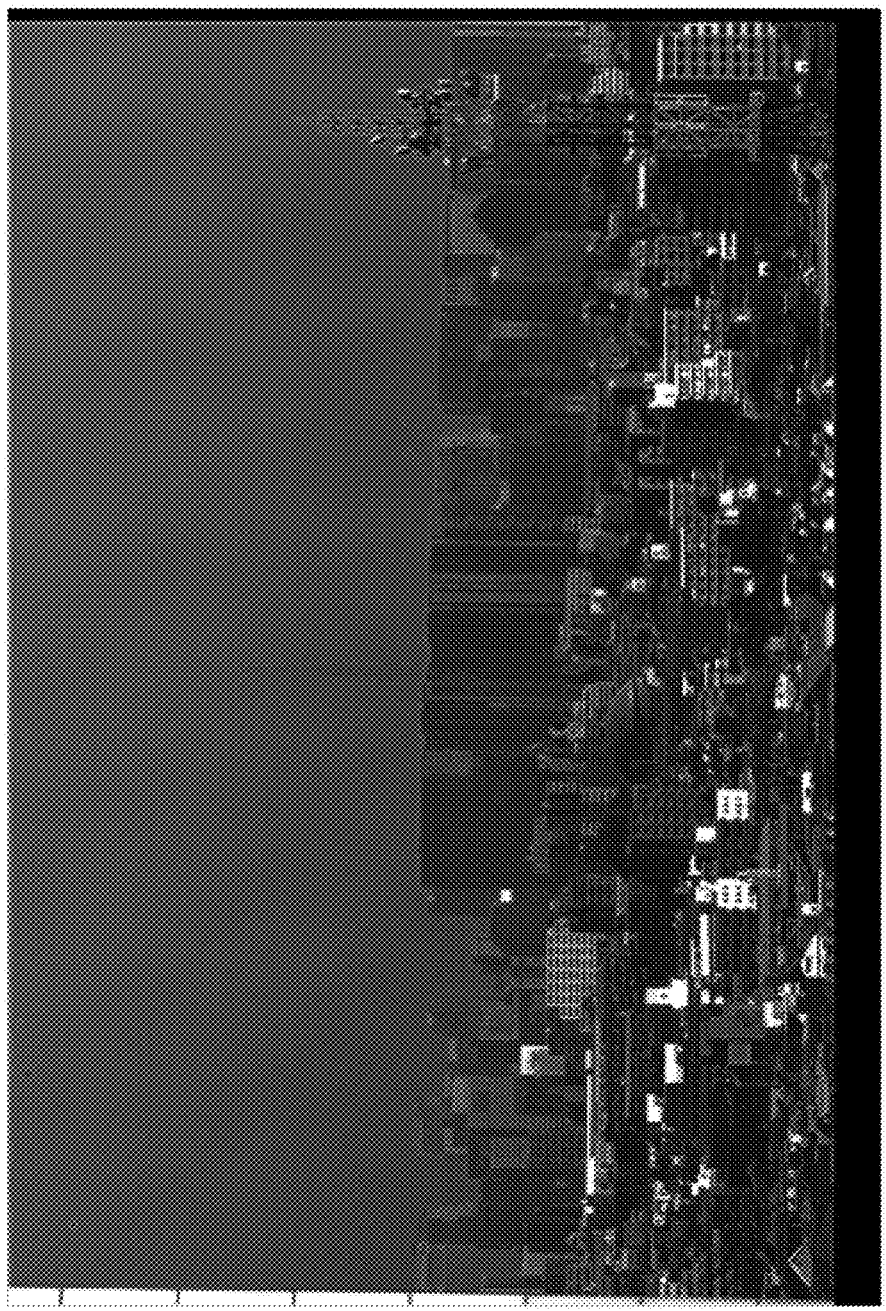
FIG. 13 is a diagram showing an example of an image (output image) after haze removal processing.

Then, by integrating the combined image $J_{comb}$ for each plane which is found into one, the final output image (haze removed image) is obtained. FIG. 13 shows the output image obtained by performing the above-described combination processing for the input image in FIG. 7. It is a little bit difficult to grasp from FIG. 13, but it is known that the image becomes more natural because of removal of scattered components caused by fine particles in the atmosphere.

As explained above, according to the present invention, it is possible to suppress the processing load while securing real-time properties of the image processing to improve visual recognizability of a captured image whose visual recognizability has been reduced by the influence of fine particle components. Then, it is made possible to obtain an image of high image quality whose visual recognizability has been improved by increasing the contrast reduced by the influence of fine particles in the atmosphere in a more natural form.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment (s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the present invention, it is possible to suppress the processing load while securing real-time properties of the image processing to improve visual recognizability of a captured image whose visual recognizability has been reduced by the influence of fine particle components.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-155791 filed Aug. 8, 2016, which is hereby incorporated by reference herein in its entirety.

What is claimed is:

1. An image processing apparatus comprising:
   one or more processors; and
   a memory having stored thereon instructions, which, when executed by the one or more processors, cause the image processing apparatus to:
   determine an atmospheric light component from a captured image including an influence of fine particles in an atmosphere; and
   generate an image from the captured image, in which the influence of fine particles has been reduced, based on the determined atmospheric light component, wherein the image is generated based on data of the captured image and data of an exposure value at the time of photographing the captured image.

2. The image processing apparatus according to claim 1, wherein
   the captured image is an image represented in an RGB color space, and
   wherein the instructions, when executed by the one or more processors, further cause the image processing apparatus to:
   determine a predetermined threshold value for a luminance value based on the exposure value;
   convert an RGB value of a pixel in the captured image into a luminance value; determine, by robust estimation processing, a pixel to estimate atmospheric light from pixels having the luminance value larger than or equal to the threshold value; and
estimate atmospheric light based on a pixel value of the determined pixel.

3. The image processing apparatus according to claim 1, wherein
the exposure value is found from a pixel value of the captured image or by measurement using a sight meter.

4. The image processing apparatus according to claim 1, wherein
the predetermined threshold value is determined by referring to a table in which different exposure values are associated with respective corresponding threshold values.

5. The image processing apparatus according to claim 1, wherein
the predetermined threshold value is determined by using a mathematical expression that specifies a relationship between the exposure value and the predetermined threshold value.

6. An image capturing device that performs image capturing of a captured image, the image capturing device comprising:
an image processing apparatus including:
one or more processors; and
a memory having stored thereon instructions, which, when executed by the one or more processors, cause the image processing apparatus to:
determine an atmospheric light component from the captured image including an influence of fine particles in an atmosphere; and generate an image from the captured image, in which the influence of fine particles has been reduced, based on the determined atmospheric light component, wherein the atmospheric light component is determined based on data of the captured image and data of an exposure value at the time of photographing the captured image.

7. An image processing method, the method comprising:
determining an atmospheric light component from a captured image including an influence of fine particles in an atmosphere; and
generating an image from the captured image, in which the influence of fine particles has been reduced, based on the determined atmospheric light component, wherein
the atmospheric light component is determined based on data of the captured image and data of an exposure value at the time of photographing the captured image.

8. A non-transitory computer readable storage medium storing a program for causing a computer to perform an image processing method, the method comprising:
determining an atmospheric light component from a captured image including an influence of fine particles in an atmosphere; and
generating an image from the captured image, in which the influence of fine particles has been reduced, based on the determined atmospheric light component, wherein
the atmospheric light component is determined based on data of the captured image and data of an exposure value at the time of photographing the captured image.

* * * * *